United States Patent [19]

Bezman

[11] 4,403,999
[45] Sep. 13, 1983

[54] PROCESS FOR PRODUCING OXYGENATED FUELS

[75] Inventor: Susan A. Bezman, Point Richmond, Calif.

[73] Assignee: Chevron Research Company, San Francisco, Calif.

[21] Appl. No.: 277,439

[22] Filed: Jun. 25, 1981

[51] Int. Cl.³ .......................... C10L 1/02; C10L 1/18
[52] U.S. Cl. ......................................... 44/56; 568/918
[58] Field of Search .................... 44/56; 568/899, 918; 585/14

[56] References Cited

U.S. PATENT DOCUMENTS

| | | | |
|---|---|---|---|
| 2,371,010 | 3/1945 | Wolfner | 44/56 |
| 2,591,672 | 4/1952 | Catterall | 44/56 |
| 2,813,908 | 11/1957 | Young | 568/918 |
| 2,827,500 | 3/1958 | Bloecher, Jr. et al. | 260/641 |
| 3,455,664 | 7/1969 | Rosscup et al. | 44/56 |
| 3,655,810 | 4/1972 | Orsay et al. | 568/512 |
| 3,793,379 | 2/1974 | Rosscup et al. | 260/641 |
| 4,154,580 | 5/1979 | Landis | 44/56 |
| 4,251,231 | 2/1981 | Baird | 44/56 |
| 4,270,929 | 6/1981 | Dang Vu et al. | 44/56 |

Primary Examiner—Jacqueline V. Howard
Attorney, Agent, or Firm—D. A. Newell; S. R. La Paglia; S. H. Roth

[57] ABSTRACT

A process for producing an oxygenated fuel composition comprising gasoline and isopropanol in which a dilute propylene feedstock is hydrated to produce isopropanol in a single pass, the unreacted olefins are oligomerized to produce gasoline blending stock and the isopropanol is added directly to the gasoline pool from a water-isopropanol azeotropic mixture without the use of energy intensive extractors.

7 Claims, 1 Drawing Figure

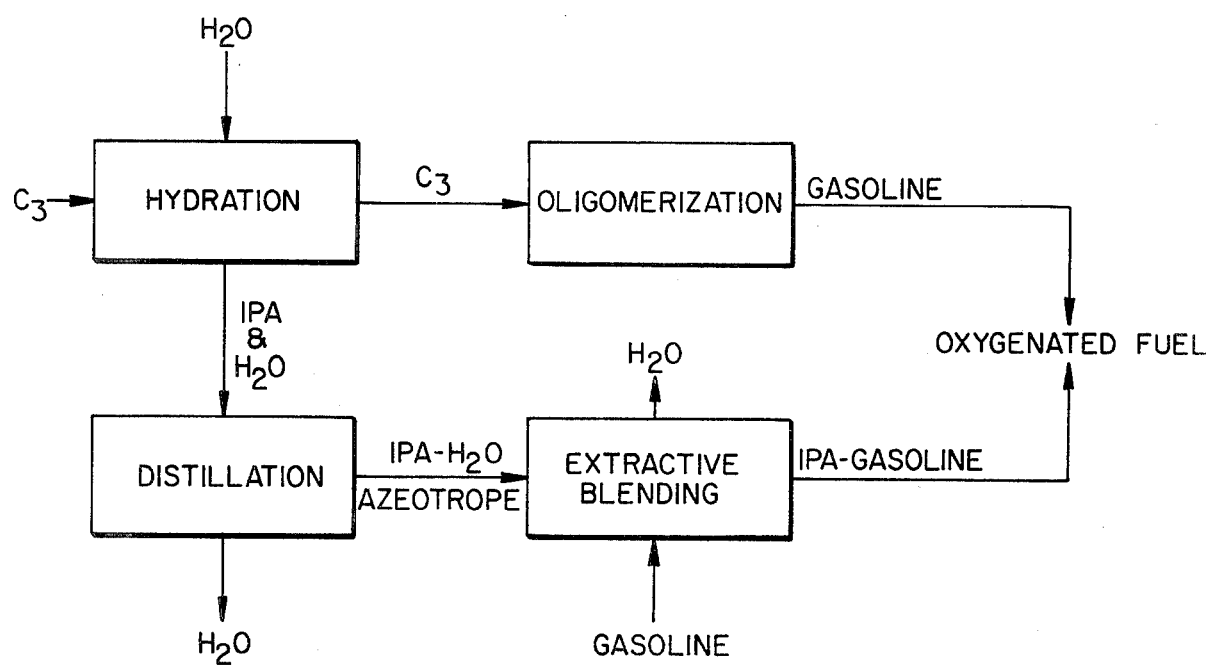

PROCESS FOR PRODUCING OXYGENATED FUELS

BACKGROUND OF THE INVENTION

The present invention relates to a process for the production of oxygenated fuel compositions. Specifically, the invention relates to a process for the production of an oxygenated fuel composition comprising gasoline and isopropanol. The present process also provides for the production of an olefinic gasoline blending stock by the oligomerization of excess olefins. It is, therefore, possible in accordance with the present invention to obtain a high octane fuel composition without the necessity for alkylation.

The process of the present invention is also more economical than prior processes, since it employs a dilute feed. In accordance with the present invention, it is possible to achieve reasonably high conversions without resorting to a costly pre-reactor $C_3=/C_3$ splitter to concentrate propylene in the feed.

As is well known, alkylation can produce a premium grade gasoline component from olefins by reaction with isoparaffins such as isobutene or isopentane. Such alkylation can be conducted thermally at high temperatures and very high pressures, but is preferably done at low temperatures in the presence of catalysts. Such catalytic alkylation proceeds quite readily and, as long as a sufficient excess of the $C_4$ or $C_5$ isoparaffin is present, results in substantially complete conversion of the olefinic feed constituents into valuable $C_7$ to $C_9$ branched chain paraffins of high antiknock value and relatively low volatility.

Refineries have, however, experienced a shortage of isoparaffins, particularly isobutane and, therefore, have an excess of olefins. So a way to place these olefins into the motor gasoline pool is needed.

At the same time, gasoline octane requirements have increased and use of the traditional lead-containing gasoline additives has been largely discontinued. It has, therefore, become necessary to find alternative means to produce high octane fuel compositions without the necessity for alkylation.

SUMMARY OF THE INVENTION

The present invention provides a process for the production of an oxygenated fuel composition and includes the steps of reacting a propylene-containing feedstock with water in the presence of a cation exchange catalyst under direct hydration conditions, oligomerizing the unreacted propylene to form an olefinic gasoline blending stock, distilling the hydration product to produce an isopropanol-water azeotrope and extracting isopropanol directly from the azeotrope into a gasoline blending hydrocarbon stream to produce an oxygenated fuel composition.

BRIEF DESCRIPTION OF THE DRAWING

The sole FIGURE is a conceptual schematic diagram of a process in accordance with the invention.

DESCRIPTION OF THE PREFERRED EMBODIMENTS

The present process involves three separate phases which, when combined, result in a highly efficient, economical means for producing a high octane fuel composition. This process enables one to employ excess $C_3$ olefins and incorporate them as high octane components into the motor gasoline pool without alkylation. The process phases are (1) direct hydration, (2) oligomerization and (3) extractive blending.

Propylene may be hydrated to the corresponding alcohol, isopropanol, by any conventional means such as disclosed in U.S. Pat. Nos. 2,813,908 and 3,793,379, incorporated by reference herein. The most preferred hydration method is that disclosed in my U.S. patent application entitled "Propylene Hydration," filed concurrently herewith, and which is incorporated by reference herein.

Briefly, the most preferred hydration method employs a feedstock comprising $C_3$ hydrocarbons having a propylene content of from about 60% to 85%. Preferred is a feed such as that which could be obtained by distilling off a $C_3$ cut from a fluid catalytic cracker. Surprisingly, it is possible to obtain a high conversion per pass even employing such dilute feedstocks.

The feedstock containing propylene is reacted with water in the presence of a cation exchange catalyst. The catalyst is preferably a sulfonated macroreticular copolymer of styrene and divinylbenzene in the acid form. Catalysts modified by chlorination to withstand higher temperatures, such as Amberlyst XN 1011 and Amberlite XE 372, manufactured by Rohm and Haas, are particularly preferred. Other catalysts suitable for the direct hydration of propylene and methods for their preparation are described in U.S. Pat. No. 2,813,908, incorporated by reference herein.

In the direct hydration step, the propylene-containing feedstock is mixed with water in a ratio of water to propylene from about 5 to 15, preferably from about 8 to 12, and most preferably about 8. The mixture is then fed to a reactor, preferably in a downflow, trickle bed configuration to contact the catalyst.

Hydration conditions may include a pressure of from about 1,000 to 2,000 psig, preferably 1,400 to 1,500 psig and a temperature of from about 275° to 375° F., preferably from about 290° to 355° F. The conditions are selected so that the propylene is in a supercritical gas phase and the water is primarily in the liquid phase. Finally, the propylene liquid hourly space velocity is from about 0.15 to about 1.5 per hour, preferably from about 0.4 to 0.5 per hour.

In the direct hydration stage, the percent propylene conversion should be maintained at a predetermined level, generally from about 50% to 90%, preferably about 67%. To do so, the temperature in the reactor should be raised incrementally to compensate for the loss of catalyst activity during the course of the reaction.

The crude product which emerges from the bottom of the reactor contains water, isopropanol, diisopropyl ether (a by-product), propylene and propane as well as any $C_4$ hydrocarbons present in the feed or traces of alcohols or ethers derived from reactions of $C_4$ hydrocarbons in the reactor. This crude product is passed through one or more conventional gas-liquid separators to separate the gases, i.e., propane, unreacted propylene and trace $C_4$ and lower hydrocarbons from the liquids, i.e., isopropanol, water and diisopropyl ether.

The separated gases generally contain at least 40% unreacted $C_3$ olefins. Such olefins, of course, may be fed to a conventional alkylation plant where they are allowed to react with isoparaffins in the presence of a suitable catalyst such as HF or sulfuric acid. The resultant alkylation product, presumably a mixture of high-branched C₇ paraffins is a high octane product suitable for direct addition to the motor gasoline pool. As discussed, the desirability of alkylation is limited by the shortage and high expense of the requisite isobutane.

The propylene obtained from the overhead of the liquid-gas separator are catalytically oligomerized in accordance with the invention to make olefinic gasoline, a high octane gasoline pool component. Such oligomerization obviates the need to alkylate excess olefins, significantly reducing the process cost.

The catalytic oligomerization of the $C_3$ gases may be conducted in any of the known and conventional manners. For example, in U.S. Pat. No. 3,431,317, incorporated by reference herein, propylene is polymerized to its dimer and higher weight oligomers by using an alkyl aluminum dichloride catalyst at temperatures within the range of 30° to 100° C. and at pressures of 30 psi to the saturation pressure of propylene.

U.S. Pat. No. 3,483,269, incorporated by reference herein, discloses olefin oligomerization in the presence of a heterogeneous catalyst composition comprising a π-allyl nickel halide on an inorganic oxide catalyst support.

U.S. Pat. No. 3,773,853, incorporated by reference herein, teaches oligomerization with a catalyst comprising a tantalum-containing compound at temperatures from ambient to 250° C. and at pressures from about 1 to 160 atmospheres.

Oligomerization may be conducted using a liquid phosphoric acid catalyst as disclosed in commonly assigned U.S. Pat. No. 3,887,634, incorporated by reference herein. In addition, propylene may be oligomerized using a solid catalyst consisting essentially of a silica carrier and phosphoric acid having a molar ratio of $P_2O_5$ to $SiO_2$ of between 0.6 and 0.95 and a content of crystalline form of silicium phosphate between 75% and 95%, as disclosed in U.S. Pat. No. 3,758,627, incorporated by reference herein.

Other suitable oligomerization catalysts and reaction conditions are described in U.S. Pat. Nos. 3,642,932; 3,855,341; 3,907,923; 3,932,553; 4,017,553; 4,024,203; and 4,098,839, all of which are incorporated by reference herein.

As another example, the Dimersol process disclosed in the Oil & Gas Journal of April 28, 1980, pages 77–83, incorporated by reference herein, is a catalyzed liquid phase dimerization of propylene. In this process, the charge stock may also contain propane, so the $C_3$ gases may be used.

In the Dimersol process, the reactor is operated at sufficient pressure to keep all the $C_3$'s liquid at near ambient temperatures. The catalyst, which is soluble in the feed, is injected into the feed line to the unit. The reactor operates liquid-full which provides residence time for the catalyst to contact the feed and for the reaction to take place. The exothermic heat of 300 BTU/lb of converted propylene is removed by circulation through an air-cooled heat exchanger. The recycle rate is many times that of the heat rate, but depends only on maintaining isothermal conditions. Typical catalysts that may be employed in this process are nickel carboxylate-alkyl aluminum halide combinations as disclosed in French Pat. No. 2,438,084, incorporated by reference herein.

The crude liquid product from the hydration stage which contains water, isopropanol, diisopropyl ether and perhaps traces of $C_4$ olefin-derived ethers and/or alcohols, is generally caustic neutralized. This product is then passed through a first distillation column which is generally operated at near atmospheric pressure at a temperature so that the product taken overhead is primarily diisopropyl ether (actually the low-boiling azeotrope which also contains 4% isopropanol and 5% water, b.p. 62° C.). The bottoms from this first distillation column, containing primarily isopropanol and water, are passed through a second distillation column. The overhead from the first column, primarily diisopropyl ether, may be blended into gasoline directly, since diisopropyl ether has a high octane number.

The second distillation column containing the isopropanol and water, is operated generally at or near atmospheric pressure and at a temperature such that the isopropanol-water azeotrope (b.p. 80° C.) having the composition of 87.8 weight percent isopropanol and 12.2 weight percent water is taken overhead. The column bottoms which consist primarily of a very dilute aqueous salt solution may be either (a) desalted by treatment with an ion exchange resin and the pure water recycled with make-up water to the hydration reactor or (b) discarded.

In the third phase of the present process, extractive blending, isopropanol is separated from the isopropanol-water azeotrope and simultaneously blended with a gasoline blending hydrocarbon stream resulting in an oxygenated fuel-containing blending stock which can be used directly in the motor gasoline pool. The method of the present invention eliminates the necessity for employing energy intensive "extractors" and provides a simple, economical way to introduce isopropanol from an isopropanol-water azeotrope directly into a gasoline blending stock. This extractive blending technique is the subject of my U.S. patent applications entitled "Extractive Blending Process," "Continuous Extractive Blending Process" and "Improved Extractive Blending Process," filed concurrently herewith and incorporated by reference herein.

Briefly, the azeotrope is dehydrated by combining it with a gasoline blending hydrocarbon stream. The gasoline blending hydrocarbon may be any hydrocarbon that can be added to the motor gasoline pool including straight run, alkylate, FCC gasoline, reformate or their mixtures such as Chevron Unleaded Regular gasoline (ULR). The gasoline blending hydrocarbon may also comprise diesel and/or jet fuels. The mixing may be done in a mixing tank, but is preferably accomplished by use of inline mixers such as the pipe mixers manufactured by Komax Systems, Inc. as opposed to the energy intensive extractors. From about 2 to 15 volumes of hydrocarbon per volume of azeotrope, preferably at least 10 volumes are employed. A milky emulsion forms on mixing. This emulsion is separated rapidly into two phases, for example, by passing it through a commercial water filter coalescer such as a Racor Model 2000 SM Filter Separator, preferably after modification to avoid deterioration of polymeric components. Other such separators are available from Facet Enterprises, Inc.

The water in the emulsion may be coalesced by employing any conventional water coalescer means including coalescers, separating membranes and certain electrical devices.

Coalescers are generally mats, beds or layers of porous or fibrous solids whose properties are especially suited for the purpose at hand. Their action appears to be two-fold: (1) protective, high-viscosity films surrounding the dispersed-phase droplets are ruptured and wiped away by the coalescers; (2) the droplets preferentially wet the solid, attach themselves thereto, and grow in size by coalescing with others similarly caught. The enlarged drops are then carried away by the flowing stream of continuous phase. The coalescer is, therefore, generally a solid of large surface to volume ratio, with uniformly small passages to ensure action on all the dispersion, of low pressure drop for flow, and for best results it should be preferentially wet by the dispersed phase. A coalescer should also be mechanically strong enough to resist the pressure drop prevailing, and chemically inert toward the liquids. Beds of granular solids, such as sand and diatomaceous earth, and bats of excelsior, steel wool, copper turnings, glass wool, fiberglass, and the like have been used. Materials such as mineral wool may be coated with substances such as silicones and resins to provide the preferential wetting characteristics.

Water coalescers and methods for resolving water and oil emulsions are disclosed in U.S. Pat. Nos. 2,288,532, 2,522,378 and 2,746,607, which are incorporated by reference herein.

If the capillary size of a porous substance is very small, then the liquid which preferentially wets the solid may flow through the capillaries readily, but strong interfacial films block the capillaries for flow of non-wetting liquid. Sufficient pressure will cause disruption of the films and permit passage of the non-wetting liquid, but regulation of the pressure commensurate with the pore size permits perfect phase separation. Separating membranes of this type are generally made of a variety of materials such as procelain, resin-coated paper, and the like, and may be either hydrophilic or hydrophobic in character. They are generally made thin to permit maximum passage of the wetting liquid. In practice, the dispersion usually first passed through a coalescer to relieve the load on the membrane.

Subjecting electrically-conducting emulsions or dispersions to high-voltage electrical fields may cause rupture of the protective film about a droplet and thus induce coalescence. This has been used particularly for the desalting of petroleum emulsified with brine, and for similar applications. See, e.g., U.S. Pat. No. 2,527,690, incorporated by reference herein.

For a 10:1 volume ratio, regardless of the rate of separation, the hydrocarbon layer composition is about 91.2 weight percent gasoline, 8.3 weight percent isopropanol and 0.41 weight percent water. The aqueous phase consists essentially of about 75% water and 25% isopropanol. This layer represents only a small volume of material, however, (less than 0.1) and may be recycled to the second distillation column. The isopropanol-hydrocarbon phase emerging from the coalescer can be blended with additional gasoline or used directly as automotive fuel without further treatment.

EXAMPLE I

A catalyst charge of Rohm and Haas Amberlite XE 372 having a volume of 10 cc when swollen in water was loaded into the mid-section of a ⅜" O.D. telfon coated 316 stainless steel reactor tube. Two beds of 20 to 32 mesh alundum particles which were each 5" long were placed in the reactor, one above and one below the catalyst bed to provide for mixing of the reagents. Water and a liquified $C_3$ cut from a fluid catalytic cracker were fed concurrently into the top of the reactor tube at the rates of 12 cc and 6 cc liquid per hour, respectively, which corresponds to a molar ratio of water to propylene of 12:1. The $C_3$ cut had the following composition in weight percent:

| | |
|---|---|
| propylene | 76.9 |
| propane | 16.8 |
| isobutane | 4.06 |
| isobutene | 0.93 |
| i-butene | 0.56 |
| trans-2-butene | 0.30 |
| n-butane | 0.19 |
| cis-2-butene | 0.15 |
| ethane | 0.08 |

The reactor was maintained at a temperature of 293° F. and a pressure of 1,440 psig. A propylene conversion of 69% was achieved. Propylene selectivities were about 90% to isopropanol and about 10% to diisopropyl ether.

Although the present invention has been described with respect to one embodiment, many modifications and variations of the present invention are possible in light of the above teachings. It is therefore to be understood that within the scope of the appended claims, the invention may be practiced otherwise than as specifically described.

I claim:

1. A process for the production of an oxygenated fuel composition comprising:
    (a) reacting a feedstock comprising propylene with water in the presence of a cation exchange catalyst under direct hydration conditions;
    (b) separating the resulting product into a first stream comprising isopropanol and water and a second stream comprising propylene;
    (c) contacting the second stream with an acid catalyst under oligomerization conditions in a second reaction zone to form an olefinic gasoline blending stock;
    (d) distilling the first stream to produce a third stream consisting essentially of a water-isopropanol azeotrope;
    (e) mixing the third stream at atmospheric pressure and ambient temperature with a fourth stream consisting essentially of a gasoline blending hydrocarbon stream;
    (f) passing the resulting mixture through water coalescer means to rapidly coalesce water out of the mixture; and
    (g) recovering an organic phase which is an oxygenated fuel composition comprising an isopropanol-containing gasoline blending hydrocarbon stream.

2. The process of claim 1, wherein the feedstock is a $C_3$ hydrocarbon stream having a propylene content of from about 60% to 85% by weight.

3. The process of claim 1, wherein the direct hydration conditions are mixed phase conditions including a temperature of from about 275° to 375° F., a pressure of from about 1,000 to 2,000 psi, a water to propylene molar ratio of from about 5 to 15, and a propylene liquid hourly space velocity of from about 0.15 to 1.5.

4. The process of claim 1, wherein the cation exchange catalyst is a sulfonated macroreticular copolymer of styrene and divinylbenzene in the acid form.

5. The process of claim 4, wherein the catalyst is in a chlorinated form.

6. The process of claim 3, wherein the mixed phase hydration conditions include a temperature of from about 290° to 350° F., a pressure of from about 1,400 to 1,500 psi, a liquid hourly space velocity of from about 0.4 to 0.5, and a water to propylene molar ratio of about 8.

7. The process of claim 1 further comprising adding the olefinic gasoline blending stock of step (c) to the oxygenated fuel composition of step (g).

* * * * *